(12) United States Patent
Weis et al.

(10) Patent No.: US 8,187,543 B2
(45) Date of Patent: May 29, 2012

(54) ELECTROCHEMICAL GAS SENSOR WITH A HYDROPHILIC MEMBRANE COATING

(75) Inventors: Léonie Weis, Graz (AT); Dietmar Werkl, Graz (AT); Marco Leiner, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1110 days.

(21) Appl. No.: 11/106,125

(22) Filed: Apr. 14, 2005

(65) Prior Publication Data

US 2005/0249885 A1 Nov. 10, 2005

(30) Foreign Application Priority Data

Apr. 26, 2004 (EP) .................................... 04009818

(51) Int. Cl.
*G01N 27/40* (2006.01)
(52) U.S. Cl. .......................................... 422/98; 422/83
(58) Field of Classification Search ............... 427/443.2; 204/431, 410, 411, 421–429; 205/781, 783.5–785, 205/787; 73/23.21, 23.32; 422/83–98; 436/68, 436/137
See application file for complete search history.

(56) References Cited

U.S. PATENT DOCUMENTS

| | | | | |
|---|---|---|---|---|
| 3,649,505 | A | * | 3/1972 | Stricker et al. ................ 204/415 |
| 3,874,850 | A | | 4/1975 | Sorensen et al. |
| 4,269,685 | A | | 5/1981 | Parker |
| 4,492,622 | A | * | 1/1985 | Kuypers .................... 204/403.07 |
| 4,534,355 | A | * | 8/1985 | Potter ........................... 600/360 |
| 4,752,426 | A | | 6/1988 | Cho |
| 4,880,883 | A | * | 11/1989 | Grasel et al. ................... 525/454 |
| 4,885,077 | A | * | 12/1989 | Karakelle et al. ......... 204/403.06 |
| 5,212,000 | A | | 5/1993 | Rose et al. |
| 5,322,063 | A | | 6/1994 | Allen et al. |
| 5,496,521 | A | * | 3/1996 | Leiner ........................ 422/82.05 |
| 5,728,762 | A | | 3/1998 | Reich et al. |
| 5,932,200 | A | | 8/1999 | Reich et al. |
| 6,001,067 | A | | 12/1999 | Shults et al. |
| 6,080,583 | A | | 6/2000 | Von Bahr |
| 6,370,941 | B2 | * | 4/2002 | Nakamura et al. ........... 73/31.05 |
| 6,432,510 | B1 | | 8/2002 | Kim et al. |
| 6,444,324 | B1 | | 9/2002 | Yang et al. |

(Continued)

FOREIGN PATENT DOCUMENTS

EP 0379156 7/1990

(Continued)

OTHER PUBLICATIONS

Kim, S.R., "Surface Modification of Poly(tetrafluoroethylene) Film by Chemical Etching, Plasma, and Ion Beam Treatments", Journal of Applied Polymer Science, vol. 77, 1913-1920 (2000).

(Continued)

*Primary Examiner* — J. Christopher Ball
(74) *Attorney, Agent, or Firm* — McDonnell Boehnen Hulbert & Berghoff LLP

(57) ABSTRACT

An electrochemical gas sensor is provided comprising a gas-permeable and substantially ion- and liquid-impermeable membrane for separating an aqueous outer solution and an inner electrolyte solution comprising a gas-permeable film of a hydrophilic polymer consisting essentially of non-covalently cross-linked polymer chains, wherein the film is present directly at least on the side of the membrane facing the aqueous outer solution, which has a surface wettability for the aqueous outer solution that is higher than the surface wettability of the membrane for the aqueous outer solution.

16 Claims, 2 Drawing Sheets

U.S. PATENT DOCUMENTS

| | | |
|---|---|---|
| 6,447,835 B1 | 9/2002 | Wang et al. |
| 6,509,148 B2 | 1/2003 | Cha et al. |
| 6,586,038 B1 | 7/2003 | Chabrecek et al. |
| 2004/0062854 A1 | 4/2004 | Jan et al. |
| 2005/0054774 A1 | 3/2005 | Kangas |
| 2005/0255579 A1 | 11/2005 | Weis et al. |

FOREIGN PATENT DOCUMENTS

| | | | |
|---|---|---|---|
| EP | 1106363 | | 6/2001 |
| GB | 2096324 | * | 4/1982 |
| JP | 2000-202907 | | 7/2000 |
| WO | WO 94/06485 | | 3/1994 |
| WO | WO 01/33195 A1 | | 5/2001 |
| WO | WO 02/070590 A2 | | 9/2002 |

OTHER PUBLICATIONS

Linek, V., Vacek, V., Sinkule, J., Beneš, P., Chalmers, R. A., "Measurement of Oxygen by Membrane-Covered Probes: Guidelines for Applications in Chemical and Biochemical Engineering", Ellis Horwood Limited, 1988.

* cited by examiner

ELECTROCHEMICAL GAS SENSOR WITH A HYDROPHILIC MEMBRANE COATING

CROSS-REFERENCE TO RELATED APPLICATION

This application claims priority to European Patent Application No. 04 009 818.8 filed Apr. 26, 2004, the disclosure of which is incorporated herein by reference.

BACKGROUND OF THE INVENTION

The present invention is directed to electrochemical gas sensors and, more particularly, to electrochemical gas sensors with a hydrophilic membrane coating.

In electrochemical gas sensors, which are also referred to as gas-selective or gas-sensitive electrodes, the gas molecules to be determined diffuse through a gas-permeable and substantially liquid- and ion-impermeable membrane from a usually aqueous outer solution or even a gas phase into the inner electrolyte space of the sensor. In addition to an inner electrolyte solution, this inner electrolyte space also contains electrodes for the electrochemical determination of the gas and, in particular, measuring electrodes or working electrodes, counterelectrodes or reference electrodes. The actual electrochemical detection reactions for determining the gas occur in this inner electrolyte space usually by means of amperometric or potentiometric methods.

A frequently used gas sensor is for example the oxygen sensor according to Clark. In this case, a gas-permeable membrane separates the inner electrolyte solution from the aqueous outer medium, the measuring medium. In the simplest case two electrodes dip into the inner electrolyte solution, one of which is arranged as a working electrode directly behind the membrane. After a polarization voltage of a suitable magnitude has been applied, the oxygen which has diffused from the measuring medium through the membrane into the inner electrolyte space is reduced at the working electrode and a current flows that corresponds to the turnover. This current is proportional to the partial pressure of oxygen in the measuring medium and is the primary measured quantity. In addition to sensors with two electrodes, those with three electrodes are also commonly used which are operated potentiostatically, whereby the additional electrode assists as a reference electrode in the stabilization of the working point.

Other widespread electrochemical gas sensors which have such gas-permeable membranes are for example sensors of the Severinghaus type for the determination of carbon dioxide or electrochemical sensors for determining hydrogen by means of oxidation on platinum electrodes.

Such electrochemical gas sensors are often used in medical and diagnostic analytical systems to determine gas partial pressures or gas concentrations in liquids. In particular, such electrochemical gas sensors are used in blood gas analyzers which play a major role in diagnostics. Blood gas analyzers often have several sensors connected in series for various parameters. The sample liquid flows through these sensors and the measurement is often carried out in a so-called stop flow procedure in which the sample rests at the time of measurement. Such systems are often used routinely in hospitals, laboratories and doctor's offices and hence high demands are made on their sensors with regard to lifetime, accuracy and reproducibility.

When gaseous analytes in aqueous solutions are determined by means of electrochemical gas sensors, in particular in physiological liquids such as, for example, whole blood, serum or urine, problems can occur in rare cases in the sample measurement or in the calibration or quality control when the sample or the quality control or calibration agent only incompletely fills the sample channel or when gas bubbles such as air bubbles are in the solution in the area of the sensors. Gas bubbles can lead to measurement errors especially in blood gas analytical systems with sensor elements for small sample volumes. Thus, an effective check has to be carried out with regard to the presence or absence of gas bubbles. However, this often requires elaborate and complicated detection methods for detecting gas bubbles in the sensor area such as those described for example in WO 01/33195 (Taagaard et al.). Gas bubbles typically get stuck on the membrane surface. This phenomenon is observed when the aqueous liquid evades the hydrophobic surface of the membrane on one or both sides during the process of filling the sample channel. If the liquid front has the possibility of running past the side of the membrane before the membrane is completely covered with liquid, a gas bubble forms in the area of the membrane. Gas bubbles that are already present as well as those that are newly formed typically remain stuck to the membrane and are often not carried along by a current of liquid. A gas bubble adhering to the membrane or located in the immediate vicinity of the membrane results in a measuring error which cannot be recognized without additional measures for detecting the gas bubble.

SUMMARY OF THE INVENTION

It is against the above background that the present invention provides certain unobvious advantages and advancements over the prior art. In particular, the inventors has recognized a need for improvements in electrochemical gas sensors.

Although the present invention is not limited to specific advantages or functionality, it is noted that the present invention provides electrochemical gas sensors in which the risk of measuring errors due to gas bubbles in the area of the sensor membrane can be further reduced. The electrochemical gas sensors of the present invention also avoid as far as possible the attachment or formation of gas bubbles in aqueous outer solutions, in particular in sample liquids and calibration, reference or quality control solutions in the area of the membrane of the gas sensor, in particular over a long time period and/or many measurement cycles.

Further, the physical and chemical parameters of the membrane and thus of the sensor of the present invention are not substantially changed by the processes and devices used according to the invention, thus further enabling reproducible and comparable determinations. Accordingly, the present invention further reduces the risk of undiscovered measurement errors by the processes and devices for avoiding encapsulation of gas bubbles in combination with processes and devices to detect gas bubbles. Moreover, the present invention provides processes for a very simple and economical hydrophilization of surfaces, in particular of the sensors and membranes according to the invention.

In accordance with one embodiment of the present invention, an electrochemical gas sensor is provided comprising a gas-permeable and substantially ion-impermeable and liquid-impermeable membrane for separating an aqueous outer solution and an inner electrolyte solution, and a gas-permeable film of a hydrophilic polymer consisting essentially of non-covalently cross-linked polymer chains, wherein the film is present directly at least on the side of the membrane facing the aqueous outer solution, the film having a surface wettability for the aqueous outer solution that is higher than the surface wettability of the membrane for the aqueous outer solution.

In accordance with another embodiment of the present invention, a gas-permeable and substantially ion-impermeable and liquid-impermeable membrane for use in the electrochemical gas sensor described herein is provided, wherein a gas-permeable film of a hydrophilic polymer is present directly at least on the side of the membrane facing the aqueous outer solution, the film having a surface wettability for the aqueous outer solution that is higher than the surface wettability of the membrane for the aqueous outer solution and that the hydrophilic polymer consists essentially of non-covalently cross-linked polymer chains.

In accordance with still another embodiment of the present invention, a process for coating membranes as described herein with a gas-permeable film of a hydrophilic polymer is provided comprising: a) dissolving the hydrophilic polymer in an organic solvent or solvent mixture to create a polymer solution; b) applying the polymer solution to at least one side of the membrane; and c) removing the organic solvent or solvent mixture such that the hydrophilic polymer is present in the form of a thin film at least on one side of the membrane.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
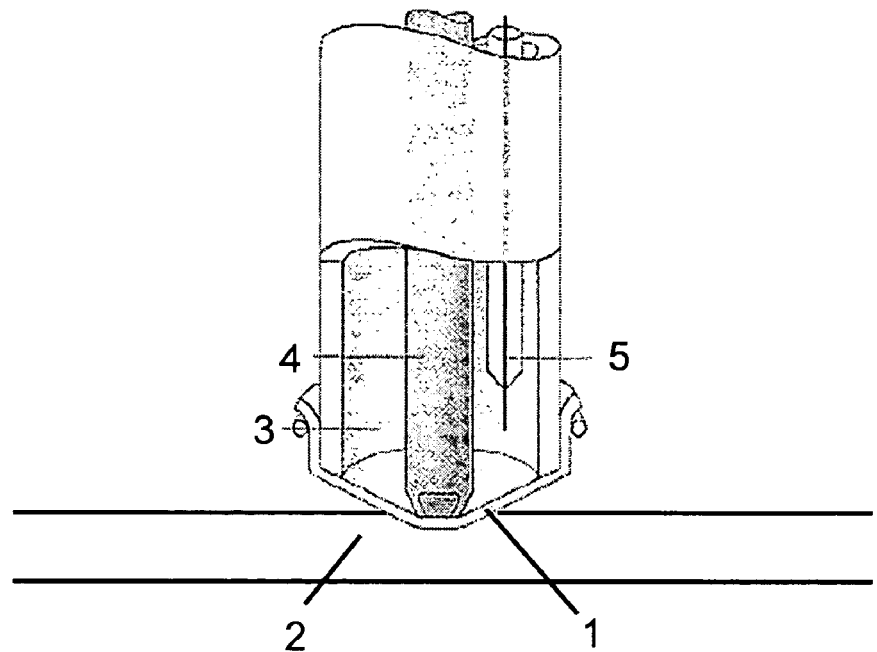
FIG. 1 shows the basic structure of an electrochemical gas sensor in accordance with an embodiment of the present invention.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

All sensory elements which enable the presence and/or partial pressure or the concentration of a gas to be examined to be determined by means of electrochemical detection methods and have a gas-permeable and substantially liquid- and ion-impermeable membrane to separate the inner electrolyte solution from the aqueous outer solution are regarded as electrochemical gas sensors or gas-selective or gas-sensitive electrodes in the sense of the present application. Amperometric or potentiometric methods can be used in particular as electrochemical detection methods. Electrochemical gas sensors in the sense of the present invention can contain other components in addition to the actual sensory components like the membrane, inner electrolyte solution or electrodes. Thus, in addition to the actual sensory components, they can contain components which serve to transport liquids or gases. Such components are for example the sample channel which adjoins the membrane and possibly other supply or discharging components to connect several sensory elements or modules in a more complex analytical system. The gas sensors according to the present invention can be used for all substances and vapours that are gaseous under normal conditions. In particular, such gas sensors according to the invention can be used to determine medically and diagnostically relevant gases. Such gases are for example oxygen or carbon dioxide.

In the sense of the present application all substances and substance mixtures that are liquid under normal conditions and have a water content of more than 50% by weight are regarded as aqueous solutions, in particular aqueous outer solutions and sample solutions. These may be solutions or homogeneous or heterogeneous mixtures such as dispersions, emulsions or suspensions. In particular, they can be sample liquids and especially body fluids and fluids derived therefrom such as blood, plasma, serum or urine. The aqueous outer solutions can also be salt solutions, buffer solutions, calibration solutions, reference solutions, quality control solutions, washing or cleaning solutions, reagent solutions or solutions containing standardized analyte concentrations, so-called standards.

A membrane or sensor membrane is understood in the sense of the present invention as a thin layer of a gas-permeable and substantially liquid- and ion-impermeable material which separates the inner electrolyte solution or the inner electrolyte space from the aqueous outer solution or the sample channel. All substances and mixtures of substances can be used in principle as membrane materials which fulfil the above-mentioned requirements. In particular, thin layers of a hydrophobic plastic can be used as membranes such as polytetrafluoroethylene, polypropylene or polyethylene. Membranes in the sense of the present invention separate two compartments in which liquids are present at least at the time of measurement. In this they differ in particular from layers that are used for detection in sensors of the thick layer type which are also referred to in some cases as membranes. Such sensors are for example described as electrochemical glucose sensors in U.S. Pat. No. 5,322,063 to Allen et al., or general electrochemical biosensors in U.S. Pat. No. 6,509,148 to Cha et al. However, the layers that are used in these cases are applied to a solid support substrate so that they are not surrounded by two compartments in which liquids are present at least at the time of measurement.

A film in the sense of the present application is understood as a continuous layer which is formed by applying a uniform layer of a substance to a substrate. The application can be carried out in particular by applying the substance to be applied in a dissolved form to the surface to be coated whereby a film is formed by removing the solvent or solvent mixture.

The term surface wettability or wettability is used in the sense of the present application as a measure for the hydrophilic or hydrophobic properties of a surface. Surfaces that can be readily wetted by aqueous liquids generally have a high hydrophilicity. The wetting angle or contact angle is specified as a measure of wettability. It is understood as the angle which a tangent on the contour of the drop makes relative to the surface of the solid body in the three phase point and which represents a measure for the wettability of the surface or interface by another phase. The smaller the wetting angle, the higher is the wettability and the more hydrophilic is the surface. A surface can be wetted by water especially when the wetting angle is less than 90°.

Hydrophilic polymers are understood in the sense of the present invention as polymeric substances which are composed of monomer building blocks of the same type or different types and have hydrophilic properties. The polymer chains of such polymers are hydrophilic or at least have hydrophilic chain sequences. Such hydrophilic polymers have chemical groups having a high affinity for water such as hydroxyl or ether groups. Examples of hydrophilic polymers are certain polyethers such as certain polyethylene glycols or certain polypropylene glycols, certain polysaccharides such as certain dextrans or certain polyalcohols such as certain polyvinyl alcohols. In particular, certain polyether-polyurethane copolymers can also be used as hydrophilic polymers. Hydrophilic polymers can be characterized on the basis of their swelling properties, for example by specifying the water uptake or expansion rate. Hydrophilic polymers in the sense of the present invention are, in particular, polymer molecules that are already polymerized and in particular long-chained polymer molecules which are not covalently cross-linked together and thus can still be dissolved in adequate amounts in suitable solvents. This differentiates the present invention from coating materials and processes in which polymer molecules that are not completely polymerized are not initially applied to a membrane but rather precursors thereof which are only then polymerized there by various methods such as plasma polymerization to form a hydrophilic network which is composed of covalently cross-linked polymer chains. In this case non-covalently cross-linked is understood to mean that the individual polymer chains are essentially not covalently linked together. However, it is basically possible that unspecific covalent bonds can form subsequently to a slight extent between individual polymer chains and/or individual polymer chains and the membrane surface after the non-covalently cross-linked polymer chains according to the invention have been applied to the surface to be coated and the polymer film has formed or form as a result of subsequent processes e.g., during storage. Such bonds that may occur unspecifically for example as a result of plasma treatment, between the individual polymer chains or between the polymer chains and membrane surface are, however, not essential for the production and/or the inventive properties of the polymer film. They can therefore be clearly differentiated from the chemical bonds between individual molecules and/or a membrane surface in the case of polymer films that are at first produced on the membrane surface from precursors where these resulting chemical bonds are essential and important for the production and properties of the polymer film that is formed.

Solvent and solvent mixtures having a water content of less than 50% by weight are regarded as organic solvents and solvent mixtures in the sense of the present application.

In accordance with the present invention, the wettability of the membrane for aqueous solutions is improved by the presence of a thin film of a hydrophilic polymer at least on the side of the membrane facing the aqueous outer solution. The physical properties of the membrane such as solubility and diffusion values for gases, extensibility, elasticity and impermeability towards substances that are not gaseous under normal conditions that are important for the function of the electrochemical gas sensor are typically not adversely affected by this.

According to the instant invention, the wettability of the membrane is increased by the presence of a thin gas-permeable film of a hydrophilic polymer at least on the side of the membrane facing the aqueous outer solution. This considerably increases the wettability for aqueous solutions in this area compared to an untreated membrane such that the risk of gas bubble inclusions in this area can be further reduced. The film of hydrophilic polymer is applied according to the invention at least on the side of the membrane facing the aqueous outer solution. The film is typically produced in such a manner that the film of the hydrophilic polymer is directly formed on the surfaces of the membrane without additional intermediate layers. In doing so the entire side of the membrane facing the aqueous outer solution can be provided with a film of the hydrophilic polymer. In other embodiments the entire side of the membrane facing the aqueous outer solution is not provided with a film of hydrophilic polymer but rather only the area of the membrane which can make contact with the aqueous outer solution. In other embodiments the entire membrane i.e., the side facing the aqueous outer solution as well as the side facing the inner electrolyte solution can also be provided with a film of the hydrophilic polymer, for example, by briefly immersing the entire membrane in a solution of the hydrophilic polymer, subsequently pulling out the membrane, and then removing the solvent.

The other requirements of not significantly changing the physical properties of the membrane are achieved according to the present invention by the hydrophilic polymer being present in the form of a very thin gas-permeable film in a typical embodiment. Depending on the type and quality of the hydrophilic polymer, the film thickness can be between about 0.01 and about 10 μm, typically between about 0.01 and about 1.2 μm, and more typically between about 0.01 and about 0.2 μm.

Amperometric oxygen sensors are used, for example, in the OMNI analytical systems of Roche Diagnostics. These are miniaturized gas sensors of the Clark type. The gas sensor elements used here comprise a sample channel for transporting and providing the sample in addition to the actual sensor with the inner electrolyte space and the electrodes located therein. A gas-permeable and substantially ion- and liquid-impermeable plastic membrane is located between the inner electrolyte space and sample channel which separates the inner electrolyte space and sample channel. In this case the membrane is present in a mechanically stretched state.

The basic construction of such an electrochemical gas sensor is shown in FIG. 1. A gas-permeable and substantially ion- and liquid-impermeable membrane 1 separates the sample channel 2 from the inner electrolyte space 3. The latter is filled with an inner electrolyte solution in which a measuring electrode 4 and a bleeder electrode 5 are located. The membrane 1 is brought into a mechanically stretched state by the measuring electrode 4.

The membrane which separates the sample channel and inner electrolyte space has to fulfil certain requirements with regard to its physical and chemical properties. Relevant properties of the membrane are in particular low solubility values and high permeability values for the gas to be determined, a high mechanical extensibility and elasticity, a substantial impermeability to substances that are not gaseous under normal conditions and, in particular, to low molecular weight charged and uncharged substances, and the highest possible chemical inertness and a high homogeneity.

Thin membranes of plastic are often used in electrochemical gas sensors whose properties are the most optimal compromise with regard to the above-mentioned requirements. Membranes with layer thicknesses in the micrometer range made of hydrophobic plastics are often used and in particular those made of polytetrafluoro-ethylene, polypropylene or polyethylene. Further information on typical membrane materials may be found in "Measurement of Oxygen by Membrane-covered Probes" (Ellis Horwood series in analytical chemistry), 1988, Ellis Horwood Limited, page 91f.

Figure 3:
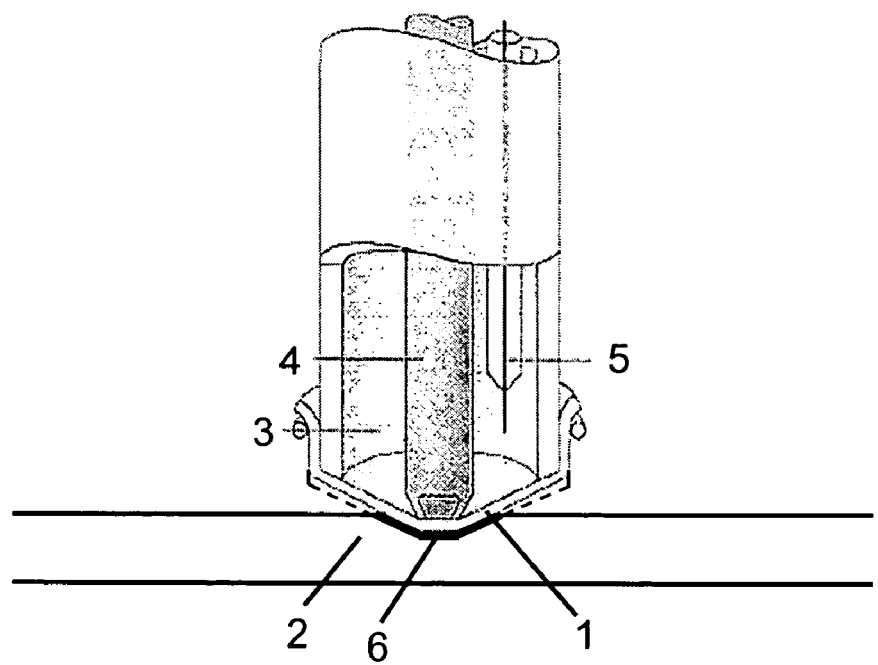
FIG. 3 shows the basic structure of an electrochemical gas sensor of FIG. 1 which has a membrane that is provided according to the invention with a film of a hydrophilic polymer.

FIG. 3 shows a schematic diagram of the basic structure of such an electrochemical gas sensor according to one embodiment of the present invention, which has a membrane provided with a film of a hydrophilic polymer. The elements 1 to 5 have already been described in connection with FIG. 1. According to the present invention, membrane 1 has a film of a hydrophilic polymer 6 on the side facing the sample channel 2. This film covers at least the part of the membrane which can make contact with the liquids in the sample channel (filled-in area). In other typical embodiments of the present invention, it is possible, especially also for production engineering reasons, that additional parts of the membrane are provided with a film of the hydrophilic polymer 6 (shaded area).

By coating a base membrane with a film of a hydrophilic polymer which is different to the material of the base membrane, it is possible to adapt the chemical and mechanical properties of this system at least partially independently of one another to match the specific requirements of the respective sensor type, for example, by specific selection of the materials or thicknesses of the base membrane and hydrophilic polymer. This allows better optimized membrane system properties to be obtained than is the case with membranes according to the prior art. In addition, the use of the membrane systems according to the present invention allows the amount of required hydrophilic polymer to be considerably reduced compared to the other membranes of the prior art since, in the present case, substantially thinner hydrophilic polymer layers in the range of a few hundred nanometers are already sufficient for an optimized hydrophilization of the surface.

In a typical embodiment of the present invention, the film applied to the membrane consists of a hydrophilic polymer which is soluble in certain organic solvents and solvent mixtures and is substantially insoluble in aqueous solutions and, in particular, in the aqueous outer solutions and sample liquids. In particular, the use of such hydrophilic polymers enables the membrane to be coated rationally and efficiently with a film of such a hydrophilic polymer in a long-lasting and durable manner without additional chemical reaction steps. The coating can for example be carried out by firstly dissolving the hydrophilic polymer in an organic solvent or solvent mixture, subsequently applying this polymer solution to the parts of the membrane to be coated, removing any excess of polymer solution such that a certain amount of polymer solution remains on the membrane, and finally removing the organic solvent or solvent mixture of the polymer solution that is on the membrane such that a film of the hydrophilic polymer remains on the membrane. In addition, it is possible to specifically define and adjust the thickness of the film of hydrophilic polymer applied to the membrane by adjusting the amount and/or concentration of the polymer solution remaining on the membrane. Hence, hydrophilic polymers can be used which are composed of non-covalently cross-linked polymer chains. These can be produced by the process described above. A major advantage of the present invention is that the hydrophilic polymer not have to be produced only on the coated membrane but rather the hydrophilic polymer chains can already be applied to the membrane in an essentially ready-to-use solution. This distinguishes the present invention especially from hydrophilic coatings that are produced by polymerizing monomers, especially by plasma polymerization, on a base membrane since the method according to the invention which uses already polymerized hydrophilic polymers that are essentially composed of non-covalently cross-linked polymer chains does not required complicated polymerization steps. The use of such hydrophilic polymers enables a hydrophilic coating to be produced directly and simply without additional chemical reaction steps. For this purpose the polymer chains do not necessarily have to be cross-linked with one another in order to achieve a durable hydrophilic coating. By using longer-chained polymers they can arrange to form a durable film of a hydrophilic polymer even without covalent cross-linkings.

The substantial insolubility of the hydrophilic polymer in aqueous solutions and especially in aqueous outer solutions and sample liquids further improves the stability of the hydrophilic polymer film. Hence, the durability of the film can be increased especially when such membranes provided with a film of a hydrophilic polymer are used in electrochemical gas sensors in diagnostic analytical systems such as blood gas analyzers. Frequent contact with aqueous solutions, for example due to the repeated process of filling and emptying the sample channel as is common in such blood gas analytical systems, can reduce the layer thickness of the film over time due to a continuous dissolution of the film of hydrophilic polymer. Such a dissolution of the polymer film can be avoided to a considerable extent by using hydrophilic polymers that are substantially insoluble in aqueous solutions so that such films have an increased life-time and are thus typically suited for use in such analytical systems.

In another typical embodiment of the present invention, the film present on the membrane comprises a polyether-polyurethane copolymer. Such polyether-polyurethane copolymers are described for example in the U.S. Pat. Nos. 5,728,762 and 5,932,200, both to Reich et al., the disclosures of which are hereby incorporated by reference for their teaching of polyether-polyurethane copolymers. Such hydrophilic polymers are surprisingly especially suitable for an inventive coating of a membrane with a film of a hydrophilic polymer. Such typical polyether-polyurethane copolymers are block copolymers with hydrophilic regions and hydrophobic regions. As a result of these amphiphilic properties the polymers dissolve well in certain organic solvents and solvent mixtures, on the other hand they organize themselves after removal of the organic solvent or solvent mixtures to form hydrogels with hydrophilic surface properties that are substantially insoluble in aqueous solutions and are thus particularly suitable for a coating according to the present invention. Such particularly suitable polyether-polyurethane copolymers can for example be obtained from CardioTech International, Inc., Woburn, Mass., USA.

In a typical form, the membrane of the present invention comprises a gas-permeable plastic such as, for example, polytetrafluoroethylene, polypropylene or polyethylene. These materials are particularly suitable for use in electrochemical gas sensors since, on the one hand, they are highly permeable to substances that are gaseous under normal conditions and, on the other hand, are substantially impermeable to substances that are not gaseous under normal conditions and thus fulfil the basic requirements for a semi-permeable membrane. Thin membranes of polytetrafluoroethylene with a layer thickness in the micrometer range are especially suitable as membranes for electrochemical gas sensors. Such membranes are characterized by extensibility and elasticity which makes them especially suitable for use as mechanically stretched membranes in electrochemical gas sensors which is illustrated schematically in FIG. 1.

In yet another typical embodiment of the present invention, the surface of the membrane is treated before the film of hydrophilic polymer is produced. For this purpose at least the part of the surface of the membrane is treated on which a film of the hydrophilic polymer is subsequently produced. In this connection it has surprisingly turned out that such a pretreatment can further improve the adhesion of the film on the membrane and the resistance of the applied film to physical and chemical stresses. Physical stress can in particular be understood as repeated contact over a long time with aqueous sample liquids and in particular with body fluids such as blood, plasma, serum or urine. Such physical stress over a long time period can reduce the layer thickness of the film of hydrophilic polymer in the course of time or the film can wholly or partially detach from the membrane. Chemical stresses can among others be contact with aggressive chemical reagents such as aggressive cleaning solutions.

Treatment of the membrane before applying the film of the hydrophilic polymer can be carried out using physicochemical methods, typically by means of plasma treatment. However, it is possible to use other physicochemical methods to pretreat the membrane such as, for example, ion beam treatment or treatment with an oxidizing substance such as, for example, a sodium naphthalene solution. Such methods for surface treatment are known and described for example in "Surface Modification of Poly(tetrafluoroethylene) Film by Chemical Etching, Plasma and Ion Beam Treatments", Kim S., Journal of Applied Polymer Science, 2000, vol. 77, p. 1913-1920 or in WO 94/06485 (Chatelier et al.). Suitable chemical methods for surface treatment are typically not those methods whereby additional intermediate layers such as bonding agent layers are applied. Rather, in accordance with the present invention, those methods are regarded as typical physicochemical methods for surface treatment which result in an increase in the reactivity of the surfaces without substantially changing the chemical composition of the membrane. Such treatment of the surface of the membrane before applying the polymer film modifies the surface in such a manner that the adhesion and resistance of the polymer film to physical and chemical stress is increased. It surprisingly turned out that treatment of the membrane with a plasma before applying the polymer solution achieves an adequate adhesion between the membrane and the polymer film as well as sufficient resistance of the film. Such a physical plasma treatment allows one to dispense with the use of toxic chemicals for surface treatment. A pretreatment of the membrane with a gas plasma results in a homogeneous modification of the surface which extends only into low depths of the membrane material. In such plasma methods for membrane pretreatment a gas plasma containing ionized particles is generated by electrical discharge or by beaming electromagnetic fields into a gas atmosphere under reduced pressure, which can be used to generate reactive areas on the membrane and thus at least to temporarily increase its reactivity such that the adhesion of the polymer film to the membrane and its resistance to physical or chemical stress can be increased.

In order to further improve the adhesion of the film on the membrane and the resistance of the applied film to physical stress, it is optionally possible to treat the membrane and the film of hydrophilic polymer applied thereto after the film of hydrophilic polymer has been made. This treatment can be in particular carried out as an additional or first plasma treatment.

In still another typical embodiment of the present invention, in addition to the membrane, other components of the electrochemical gas sensor used for liquid transport and especially the sample channel and/or other components that supply or take away liquids are provided with a film of the hydrophilic polymer at least on the side which faces the liquid. For this purpose all previously described embodiments or alternatives described in connection with the production of the film of hydrophilic polymer on the membrane can be applied in an analogous manner with regard to materials and methods to the production of the film of hydrophilic polymer on other components of the electrochemical gas sensor that are used for liquid transport. The presence of a film of hydrophilic polymer also on other components of the liquid-transporting system has the advantage that the inner surfaces of the liquid-transporting components are provided with a substantially uniform surface finish. In particular, they have a substantially uniform hydrophilic inner surface within the liquid-transporting system that can prevent discontinuities in the wetting properties and thus starting points for the attachment of gas bubbles. This reduces the risk of formation and/or attachment of gas bubbles and thus further reduces the risk of measurement errors.

The present invention also concerns processes for producing a gas-permeable film of a hydrophilic polymer on membranes of electrochemical gas sensors. These processes are characterized in that the hydrophilic polymer is firstly dissolved in an organic solvent or solvent mixture and this polymer solution is subsequently applied to at least one side of the membrane and finally the organic solvent or solvent mixture is removed so that the hydrophilic polymer is present in the form of a thin film on at least one side of the membrane. Hydrophilic polymers that are suitable for such a process according to the invention are in particular those that are soluble in certain organic solvents or solvent mixtures and are substantially insoluble in aqueous solutions and essentially in sample liquids such as blood. According to yet still another embodiment of the present invention, the film is produced by directly making the film of the hydrophilic polymer on the membrane without further intermediate layers by applying a solution of the hydrophilic polymer at least on the side of the membrane that faces the aqueous outer solution. After the solvent or solvent mixture has evaporated, the hydrophilic polymer adheres directly to the membrane as a thin film.

In yet still another typical embodiment of the present invention, the surface of the membrane is treated by physicochemical methods, typically by plasma treatment, before the polymer solution is applied. All embodiments and alternatives with regard to materials and methods that have been previously described in connection with a pretreatment of the membrane can be applied analogously to such a process.

In order that the invention may be more readily understood, reference is made to the following examples, which are intended to illustrate the invention, but not limit the scope thereof.

EXAMPLES

Example 1

Production of a Film of a Hydrophilic Polymer on a Plasma-Pretreated Membrane

In the following, X1 denotes a hydrophilic polymer of the polyether-polyurethane copolymer type which can for example be obtained from Cardiotech International, 78E Olympia Avenue, Woburn Mass. 01801-2057, USA as "Hydrophilic Polyether Polyurethane" and has a water uptake rate of 50% and an expansion rate by swelling of 60%.

In order to prepare a solution of the hydrophilic polymer X1, a defined amount of the hydrogel granulate X1 is dissolved in an ethanol-water mixture while stirring.

In order to pretreat the membrane a thin polytetrafluoroethylene membrane (Teflon membrane) mounted on a support is placed in a plasma apparatus of the type V15-G from the Plasmafinish Company and treated according to the manufacturer's instructions with a noble gas plasma for a few minutes at 2.45 GHz. After the plasma treatment, the plasma-treated surface of the mounted and plasma-treated Teflon membrane is immersed for a few seconds in the solution of the hydrophilic polymer X1, removed again from the solution and dried in air. This Teflon membrane provided with a film of the hydrophilic polymer X1 can now be used for incorporation in an electrochemical gas sensor.

Example 2

Detection of a Film of Hydrophilic Polymer Applied to a Membrane

A thin film of the hydrophilic polymer X1 was applied to a membrane of polytetrafluoroethylene of 25 micrometers thickness according to the process described in Example 1. This membrane coated in this manner was analysed with regard to its surface properties by means of Attenuated Total Reflection-Infrared-Spectroscopy (ATR-IF spectroscopy). This imaging technique for surface IR spectra by attenuated total reflection at interfaces allows conclusions to be made about the chemical properties of the surface of a sample at an analytical penetration depth of 0.5-5 micrometers. The examination was carried out with an Equinox 55-IR spectrometer from the Bruker Optics Company, Ettlingen, Germany. The ATR-IR spectra of FIGS. 2a-d show the results of such examinations where the wave number n in 1/cm is plotted on the x axis and the absorption in relative units is plotted on the y axis. FIG. 2a shows ATR-IR spectra of an uncoated polyfluorotetraethylene membrane (curve 1) and a layer of the pure coating material (curve 2) as a reference. Curve 1 has the typical absorption maxima of the C—F bonds of the polytetrafluoro-ethylene in a wave number range of ca. 1100-1300, whereas curve 2 has a considerably more complex absorption spectrum with characteristic absorption maxima in the wave number range of ca. 2800-3050 (primarily due to C—H bonds) and several absorption maxima in the wave number range of ca. 1000-1700 (primarily due to C—O bonds).

Figure 2B:
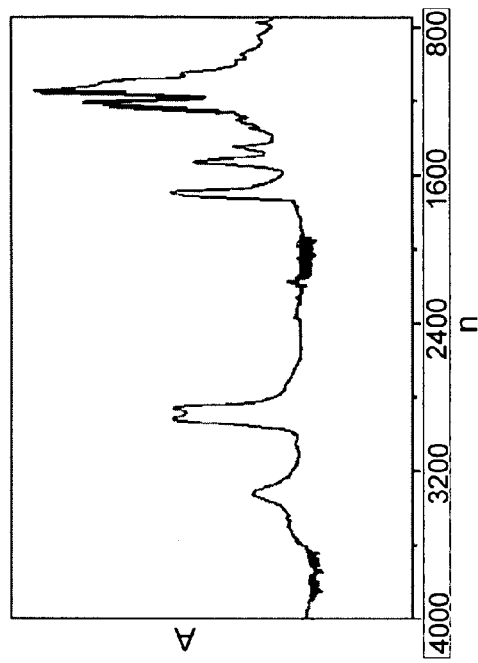
FIG. 2b shows an ATR-IR spectrum of a polytetrafluoroethylene membrane freshly coated with X1.

FIG. 2b shows an ATR-IR spectrum of a 25 micrometer thick membrane of polytetrafluoroethylene on which a thin film of the hydrophilic polymer X1 was applied according to the process described in Example 1. It can be clearly seen that this ATR-IR spectrum has the characteristic absorption maxima of the coating material in the wave number ranges of ca. 2800-3050 and of ca. 1000-1700 as well as the characteristic absorption maxima of the membrane in the wave number range of ca. 1100-1300. Considering the analytical depths of 0.5-5 micrometers, such an overlapping of the signals shows that a film of the hydrophilic polymer having a thickness in the submicrometer or in the lower micrometer range can be applied to the membrane according to the invention.

Example 3

Determination of the Surface Wettability of Uncoated Polytetrafluoroethylene Membranes and Polytetrafluoroethylene Membranes Coated with a Hydrophilic Polymer A thin film of the hydrophilic polymer X1 was applied to a polytetrafluoroethylene membrane of 25 micrometer thickness according to the process described in example 1.

The surface wettability was examined using the contact angle measuring system G2 of the Kriss GmbH, Company, Hamburg, Germany by analysing the contact angle of water on the coated and uncoated surfaces. The measurement was carried out in each case with 5 determinations on a dry surface. Table 1 shows the contact angles that were determined. The values give the mean of the 5 determinations in each case and the corresponding standard deviation.

TABLE 1

| Sample | Description | Contact Angle [°] |
| --- | --- | --- |
| 1 | polytetrafluoroethylene membrane with X1 coating | 60.8 ± 7.7 |
| 2 | polytetrafluoroethylene membrane without coating | 118 ± 7 |

The measurements clearly show that the presence of a thin film of the hydrophilic polymer X1 on the membrane can considerably reduce the contact angle and thus considerably increase its surface wettability for aqueous liquids.

Example 4

Determination of the Working Life and Durability of the Polymer Film on a Polytetrafluoroethylene Membrane A thin film of the hydrophilic polymer X1 was applied to a polytetrafluoroethylene membrane of 25 micrometer thickness according to the process described in Example 1.

This polytetrafluoroethylene membrane coated with a film of a hydrophilic polymer X1 was used as a component of an electrochemical oxygen sensor which was in operation for a period of 6 months and for at least 1000 measurements. Mainly blood and aqueous control solutions were measured in this period and other cleaning and calibration steps with different aqueous solutions were also carried out. This served as a typical stress test for the durability of the adhesion on the polymer film to the membrane and its resistance to physical or chemical stress due to the repeated exchange of aqueous liquids. After this period the membrane was subjected to an ATR-IR spectroscopy analogous to the procedure in Example 2 in order to analyse its surface properties. FIG. 2c shows an ATR-IR spectrum of a 25 micrometer thin membrane of polytetrafluoroethylene on which a thin film of the hydrophilic polymer X1 was applied according to the process described in Example 1 and which was subjected for 6 months to a stress test under the conditions described above. It can be clearly seen that this ATR-IR spectrum has the characteristic absorption maxima of the coating material in wave number ranges of ca. 2800-3050 and of ca. 1000-1700 as well as the characteristic absorption maxima of the membrane in a wave number range of ca. 1100-1300. Such an overlapping of the signals shows that a film of the hydrophilic polymer can still be detected on the membrane even after a 6-month stress test. The spectrum shown in FIG. 2c of the surface of a coated membrane after a six month stress test show, in contrast to the spectrum of the surface of a freshly coated membrane shown in FIG. 2b, differences in various absorption ranges. These differences can for example be due to the attachment of substances such as proteins from the measured sample liquids which have been deposited on the surface during the course of the 6-month stress test.

Example 5

Test for the Resistance of the Polymer Film to Aggressive Reagents

A thin film of the hydrophilic polymer X1 was applied to a polytetrafluoroethylene membrane of 25 micrometer thickness according to the process described in Example 1.

The membrane coated in this manner was placed for 24 hours at 37° C. in a cleaning solution containing 1.5% sodium hypochlorite in order to test its resistance towards aggressive chemical reagents. ATR-IR spectra of the surface of the coated membrane were recorded before and after the hypochlorite treatment and compared.

Figure 2D:
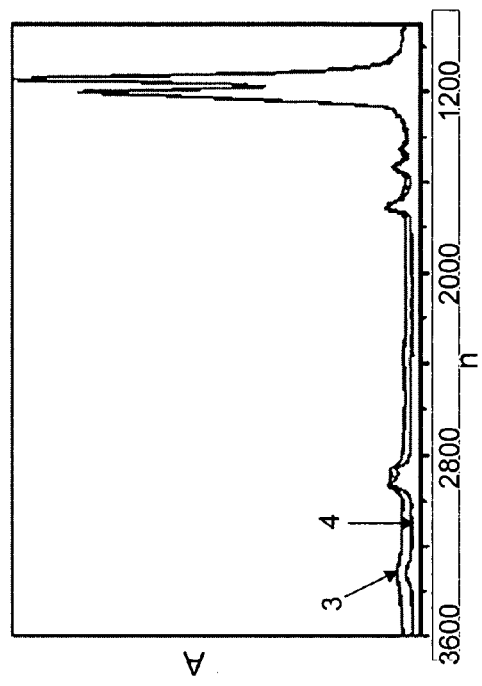
FIG. 2d shows ATR-IR spectra of a polytetrafluoroethylene membrane coated with X1 before and after a one day treatment with a hypochlorite solution.
Figure 2A:
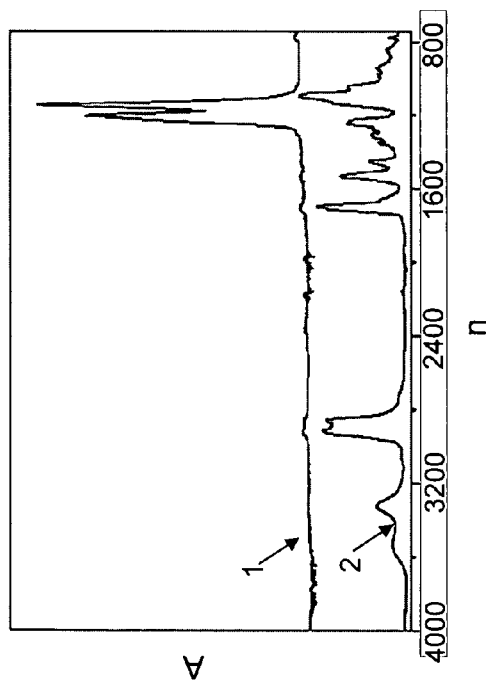
FIG. 2a shows Attenuated Total Reflection-Infrared-Spectra (ATR-IR-spectra) of an uncoated polytetrafluoroethylene membrane and of a pure layer of the hydrophilic polymer X1.
Figure 2C:
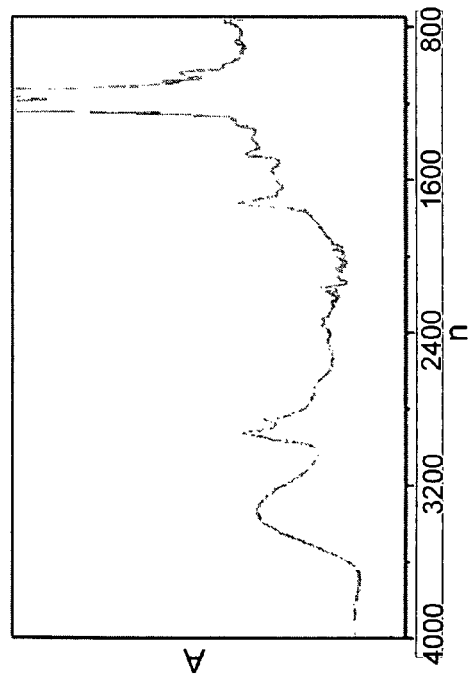
FIG. 2c shows an ATR-IR spectrum of a polytetrafluoroethylene membrane coated with X1 after a six-month stress test.

FIG. 2d shows ATR-IR spectra of the surface of the coated membrane before and after a hypochlorite treatment. Curve 3 shows the ATR-IR spectrum of the surface of the coated membrane before the hypochlorite treatment, and curve 4 shows the ATR-IR spectrum of the surface of the coated membrane after a one-day hypochlorite treatment. The spectra show almost no differences before and after treatment with such aggressive reagents. In particular, the characteristic absorption maxima of the coating material in the wave number ranges of ca. 2800-3050 and of ca. 1000-1700 are present almost completely unchanged after the hypochlorite treatment (curve 4). This shows that the film of the hydrophilic polymer adheres in a stable manner to the membrane even after a long treatment with aggressive reagents such as hypochlorite solution.

Example 6

Testing the Effectiveness of the Hydrophilic Polymer Film in Reducing the Attachment of Gas Bubbles in the Area of the Sensor Membrane A thin film of the hydrophilic polymer X1 was applied to a polytetrafluoroethylene membrane of 25 micrometer thickness according to the process described in Example 1.

Uncoated polytetrafluoroethylene membranes served as a control. The membranes coated with hydrophilic polymer and the uncoated membranes were used as components of electrochemical oxygen sensors. Samples of tonometrized blood or tonometrized aqueous control solutions were measured using these electrochemical oxygen sensors in OMNI analyzers from Roche Diagnostics. A total of about 270 samples (ca. 60% blood samples and about 40% aqueous control solutions) were measured per sensor over a period of 3 weeks. The tonometrized samples had an oxygen content which was below the atmospheric oxygen content so that filling errors could therefore be detected on the basis of a divergent measured value.

Table 2 shows a comparison of the frequency of measurement errors that are due to the attachment of gas bubbles.

TABLE 2

| | Number of oxygen determinations carried out | Number of measurement errors due to gas bubbles | Ratio of the number of measurement errors to the total number of oxygen determinations |
|---|---|---|---|
| Polytetrafluoroethylene membrane without coating | 1350 | 3 | 0.22% |
| Polytetrafluoroethylene membrane with X1 coating | 8100 | 1 | 0.012% |

Measurement errors due to gas bubbles only occurred in measurements of aqueous control solutions but in no case in measurements of blood samples and could in each case be clearly identified as measurement errors.

This clearly shows that the coating according to the present invention of the membrane of an electrochemical gas sensor with a hydrophilic polymer can reduce the risk of gas bubbles attaching in the area of the sensor membrane and thus further considerably reduce the risk of measurement errors, in the present case by 18-fold.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. An electrochemical gas sensor comprising: a gas-permeable and substantially ion-impermeable and liquid-impermeable membrane for separating an aqueous outer solution and an inner electrolyte solution, and a gas-permeable film of a hydrogel-forming hydrophilic polymer consisting essentially of non-covalently cross-linked polymer chains, wherein the film is present directly at least on the side of the membrane facing the aqueous outer solution, said film having a surface wettability for the aqueous outer solution that is higher than the surface wettability of the membrane for the aqueous outer solution, said sensor further comprising a channel for transport of said aqueous outer solution, said channel comprising at least one surface in contact with said aqueous outer solution.

2. The electrochemical gas sensor of claim 1, wherein the hydrophilic polymer is soluble in organic solvents and solvent mixtures.

3. The electrochemical gas sensor of claim 1, wherein the hydrophilic polymer is substantially insoluble in aqueous solutions.

4. The electrochemical gas sensor of claim 1, wherein the hydrophilic polymer is substantially insoluble in aqueous outer solutions.

5. The electrochemical gas sensor of claim 1, wherein the hydrophilic polymer is substantially insoluble in sample liquids.

6. The electrochemical gas sensor of claim 1, wherein the hydrophilic polymer is a polyether-polyurethane copolymer.

7. The electrochemical gas sensor of claim 1, wherein the thickness of the film of hydrophilic polymer is between about 0.01 and about 1.2 µm.

8. The electrochemical gas sensor of claim 1, wherein the thickness of the film of hydrophilic polymer is between about 0.01 and about 0.2 µm.

9. The electrochemical gas sensor of claim 1, wherein the membrane comprises a gas-permeable plastic.

10. The electrochemical gas sensor of claim 9, wherein the gas-permeable plastic is selected from polytetrafluoroethylene, polypropylene, and polyethylene.

11. The electrochemical gas sensor of claim 1, wherein the at least one channel surface in contact with said aqueous outer solution is coated with a film of the hydrophilic polymer.

12. A gas-permeable and substantially ion-impermeable and liquid-impermeable membrane for use in the electrochemical gas sensor of claim 1, wherein a gas-permeable film of a hydrophilic polymer is present directly at least on the side of the membrane facing the aqueous outer solution, said film having a surface wettability for the aqueous outer solution that is higher than the surface wettability of the membrane for the aqueous outer solution and that the hydrophilic polymer consists essentially of non-covalently cross-linked polymer chains.

13. A process for coating membranes as claimed in claim 12 with a gas-permeable film of a hydrophilic polymer, comprising: a) dissolving the hydrophilic polymer in an organic solvent or solvent mixture to create a polymer solution; b) applying the polymer solution to at least one side of the membrane; and c) removing the organic solvent or solvent mixture such that the hydrophilic polymer is present in the form of a thin film at least on one side of the membrane.

14. The process of claim 13 further comprising subjecting the surface of the membrane to a physicochemical pre-treatment prior to step b).

15. The process of claim 14, wherein the physicochemical pre-treatment is a plasma treatment.

16. An electrochemical gas sensor comprising: a gas-permeable and substantially ion-impermeable and liquid-impermeable membrane for separating an aqueous outer solution and an inner electrolyte solution, and a gas-permeable film of a hydrogel-forming hydrophilic polymer consisting essentially of non-covalently cross-linked polymer chains, wherein the film is present directly at least on the side of the membrane facing the aqueous outer solution, said film having a surface wettability for the aqueous outer solution that is higher than the surface wettability of the membrane for the aqueous outer solution, said sensor further comprising a channel for transport of said aqueous outer solution, said channel comprising at least one surface in contact with said aqueous outer solution, and wherein the thickness of the film of hydrophilic polymer is between about 0.01 and about 1.2 µm.

\* \* \* \* \*